US00PP18500P3

(12) United States Plant Patent
Dirr

(10) Patent No.: US PP18,500 P3
(45) Date of Patent: Feb. 19, 2008

(54) ***HYDRANGEA PANICULATA* PLANT NAMED 'HYPMAD II'**

(50) Latin Name: *Hydrangea paniculata*
Varietal Denomination: HYPMAD II

(75) Inventor: Michael A. Dirr, Bogart, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 11/337,938

(22) Filed: Jan. 23, 2006

(65) Prior Publication Data

US 2007/0174940 P1 Jul. 26, 2007

(51) Int. Cl.
*A01H 5/00* (2006.01)

(52) U.S. Cl. ..... Plt./250

(58) Field of Classification Search ..... Plt./250
See application file for complete search history.

*Primary Examiner*—Kent Bell
*Assistant Examiner*—June Hwu
(74) *Attorney, Agent, or Firm*—Greenlee Winner and Sullivan, PC

(57) ABSTRACT

*Hydrangea paniculata,* 'HYPMAD II' has numerous white inflorescences that mature to rose-pink. The sepals turn outward from the inflorescences at maturity resulting in a frilly, lacy appearance. The habit is compact, dense, broad-mounded, 130 cm by 170 cm in 4-years at Athens, Ga. The dark green leaves are insect and disease resistant.

6 Drawing Sheets

Botanical classification: *Hydrangea paniculata.*
Varietal denomination: 'HYPMAD II'.

BACKGROUND OF THE INVENTION

The present invention relates to a new and distinct cultivar of *Hydrangea paniculata,* a member of the Hydrangeaceae family, hereinafter referred to as 'HYPMAD II'. This cultivar is grown primarily as an ornamental for landscape use and for use as fresh cut and dried flowers. The cultivar originated from open-pollination of *Hydrangea paniculata* 'Pink Diamond' (unpatented), the pollen donor being unknown. It was selected at the University of Georgia, Athens, Ga. in 2001, from the progeny seedlings of this open pollination by continued evaluation for numerous white sepals that cover most of the interior fertile flowers, sepals that mature to rose-pink, sepals that became cupped with maturity producing a frilly, lacy inflorescence, strong stems, dark green, insect and disease resistant foliage, and compact broad rounded growth habit.

'HYPMAD II' is distinguished from its female parent 'Pink Diamond' by its numerous sepals that cover 80–90% of the interior fertile flowers. Sepals of 'Pink Diamond' cover only 40–50% of the interior fertile flowers. The sepals of 'HYPMAD II' open white, mature to rich rose-pink, and point away from the inflorescence, resulting in a frilly, lace appearance. The moderately stout stems of 'HYPMAD II' hold the inflorescences more upright than the stems of 'Pink Diamond'. 'HYPMAD II' has darker green leaves than those of 'Pink Diamond', and its develops a compact, broad-mounded habit, 130 cm by 170 cm in 4 years, whereas in side by side comparison 'Pink Diamond' was 185 cm by 185 cm at the same age.

'HYPMAD II' is distinguished from a sibling, 'HYPMAD I' (U.S. patent application Ser. No. 11/337,831) by flowering 2 weeks later, by having rose pink sepals of maturity compared to the parchment color of 'HYPMAD I', by having a more open, frilly inflorescence with only 80 to 90% of the fertile flowers being covered by the sepals, compared to the flat, completely covered inflorescence of 'HYPMAD I', and being rather larger in size, 130 cm high compared to 120 cm in side by side growth comparisons.

'HYPMAD II' holds its frilly panicles more upright than other *H. paniculta* varieties with flatter panicles, such as 'Grandiflora' (unpatented), 'Little Lamb' (PP15,395) and 'Webb's' (unpatented), and is more compact than 'Grandiflora' and 'Webb's'.

SUMMARY OF THE INVENTION

The following traits have been observed and represent the characteristics of the new cultivar. In combination these characteristics distinguish 'HYPMAD II' from all other varieties in commerce known to the inventor:

1. Abundant white flowers (sepals) that cover 80–90% of the fertile flowers producing a showy paniculate inflorescence.
2. At maturation, sepals turn rose-pink and point outward from the inflorescence producing an elegant frilly, lacy effect.
3. Compact, dense, broad-mounded growth habit, 130 cm by 170 cm in 4 years under field conditions in Athens, Ga.
4. Moderately stout stems hold inflorescences upright compared to 'Pink Diamond' and standard cultivars like 'Grandiflora' (unpatented), 'Limelight' (PP 12,874), and 'Unique' (unpatented).

'HYPMAD II' has been asexually propagated in Athens, Ga. since 2001. The characteristics of the cultivar have been stable and reproduced true-to-type in successive generations.

BRIEF DESCRIPTION OF THE PHOTOGRAPHS

BOTANICAL DESCRIPTION OF THE PLANT

Figure 1:
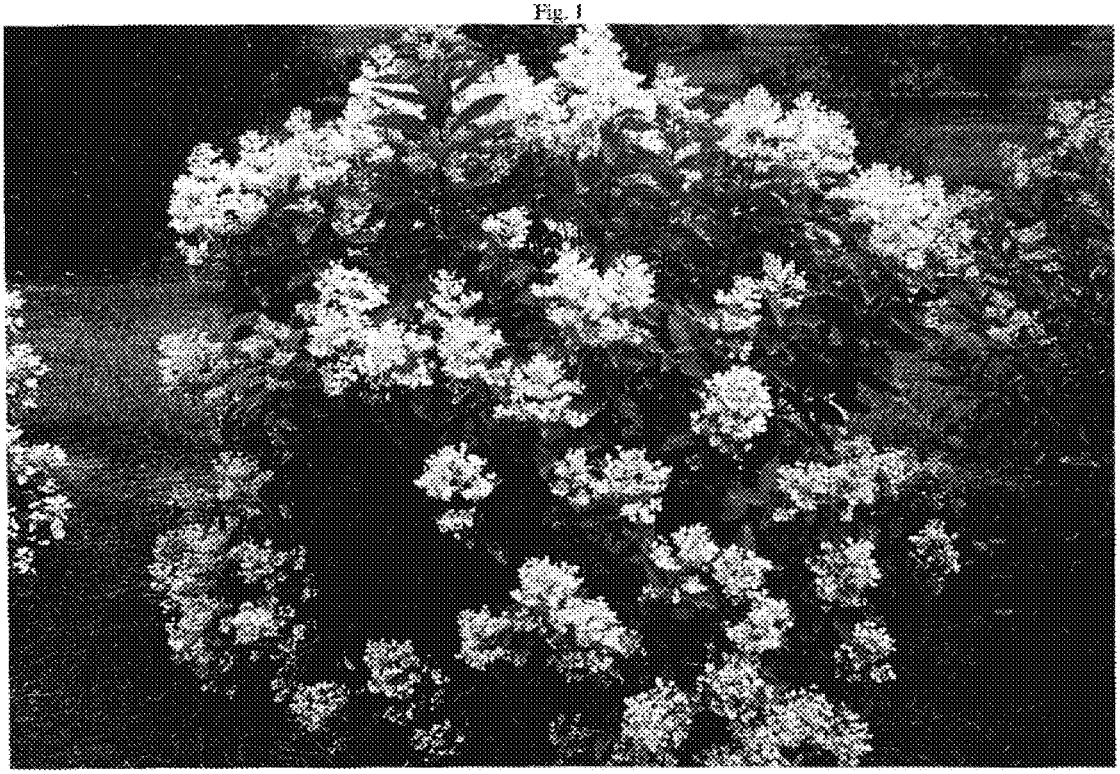
FIG. 1 shows a 4-year-old plant growing in the ground at Athens, Ga., coming into flower, Jul. 24, 2005.
Figure 2:
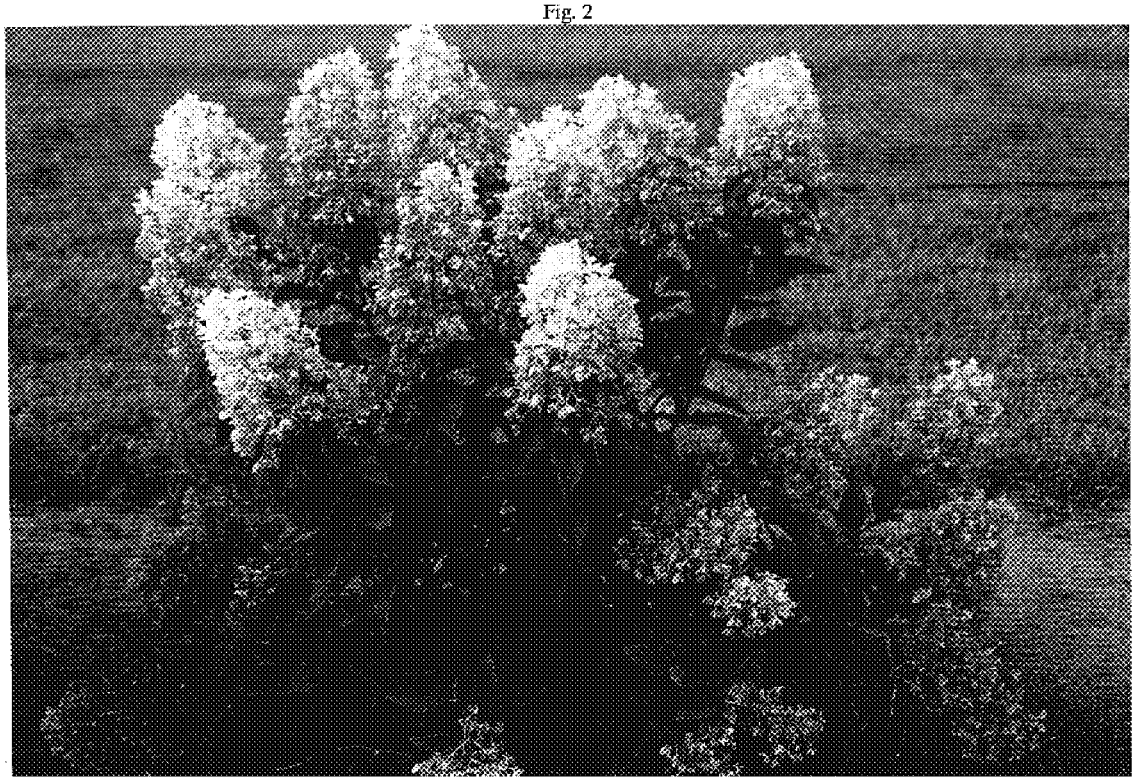
FIG. 2 shows a 3-year-old plant growing in the ground at Athens, Ga., taken Aug. 5, 2004 as inflorescences turn pink, showing the habit with strong stems.
Figure 3:
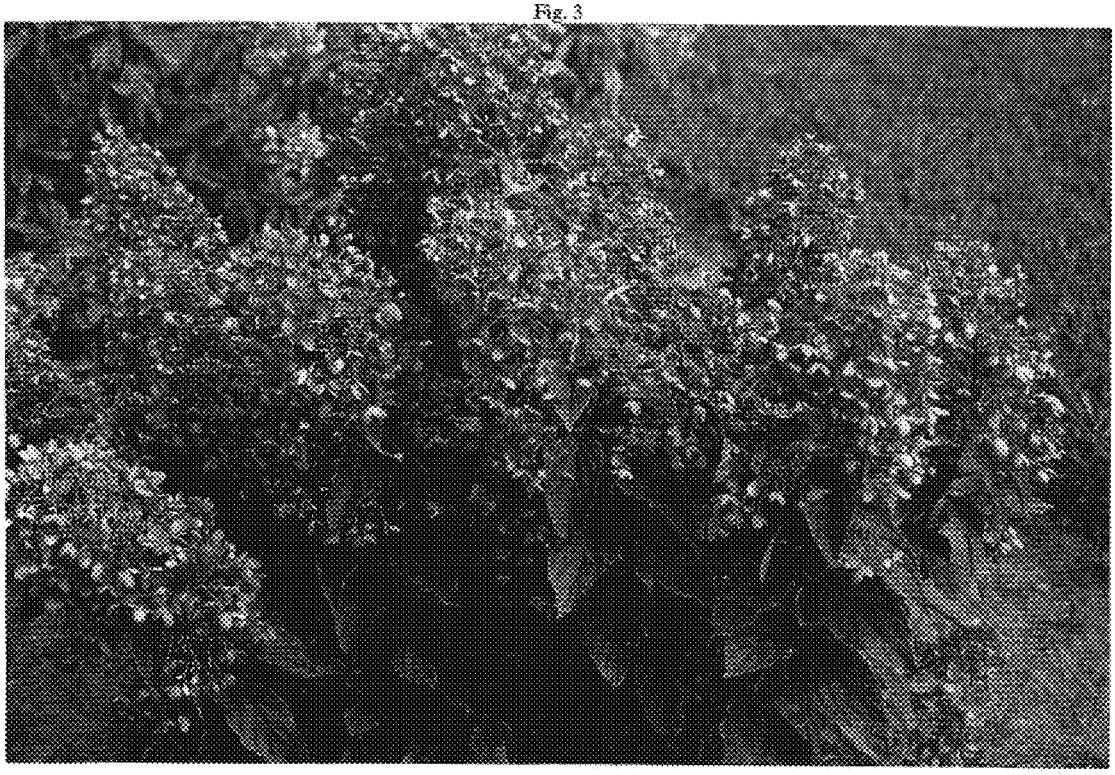
FIG. 3 shows a 3-year-old plant growing in the ground at Athens, Ga., taken Aug. 26, 2004, showing the rich, mature rose pink inflorescences and strong upright stems.
Figure 4:
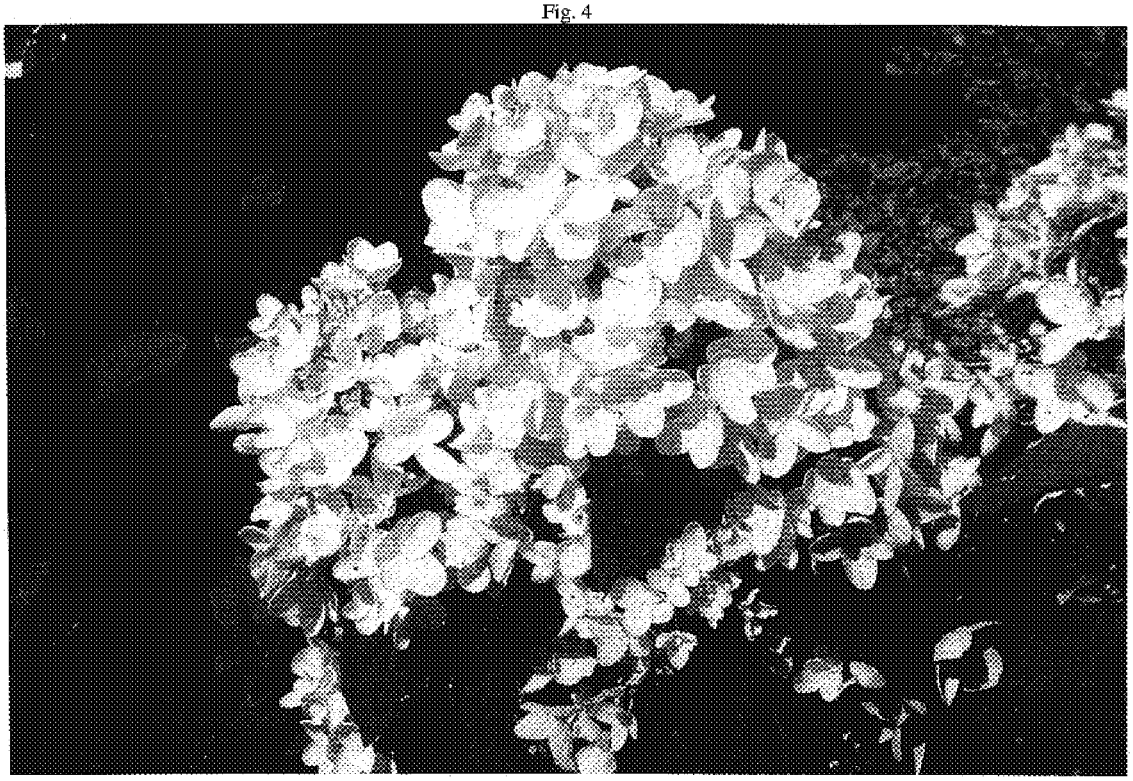
FIG. 4 shows an inflorescence, largely white with a few pink tinges, taken Jul. 16, 2005.
Figure 5:
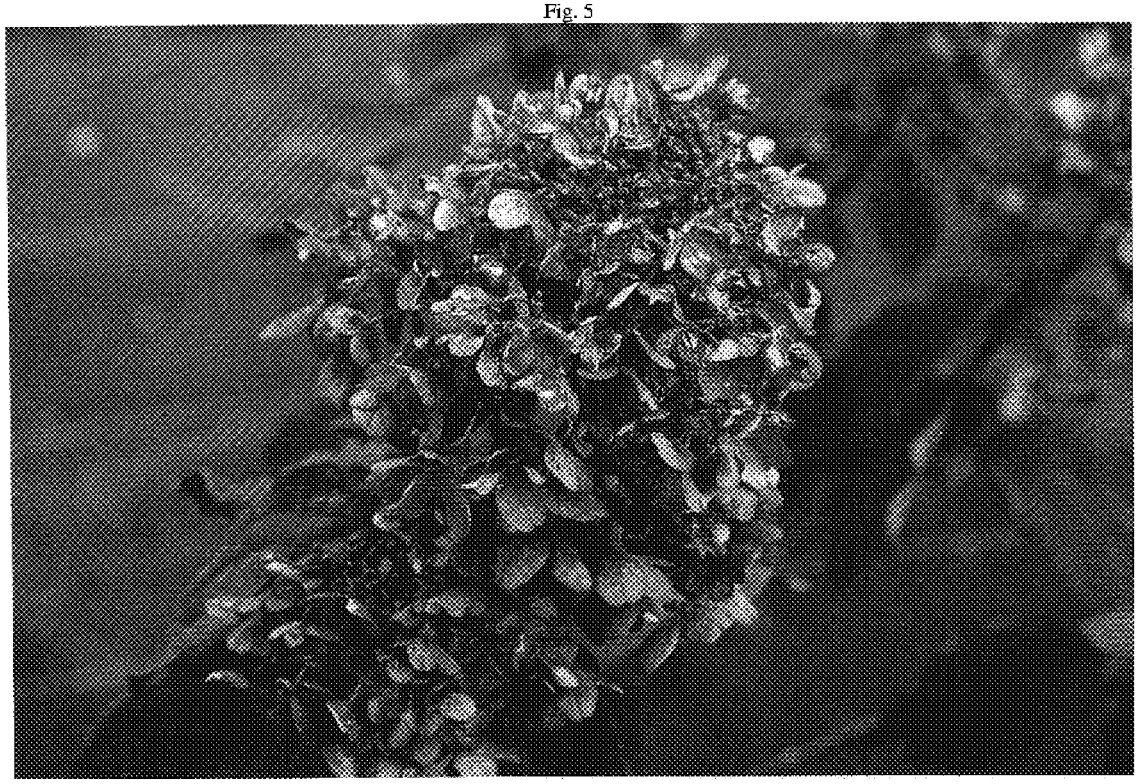
FIG. 5 shows a mature rose-pink inflorescence showing the orientation of the sepals, taken Oct. 28, 2005.
Figure 6:
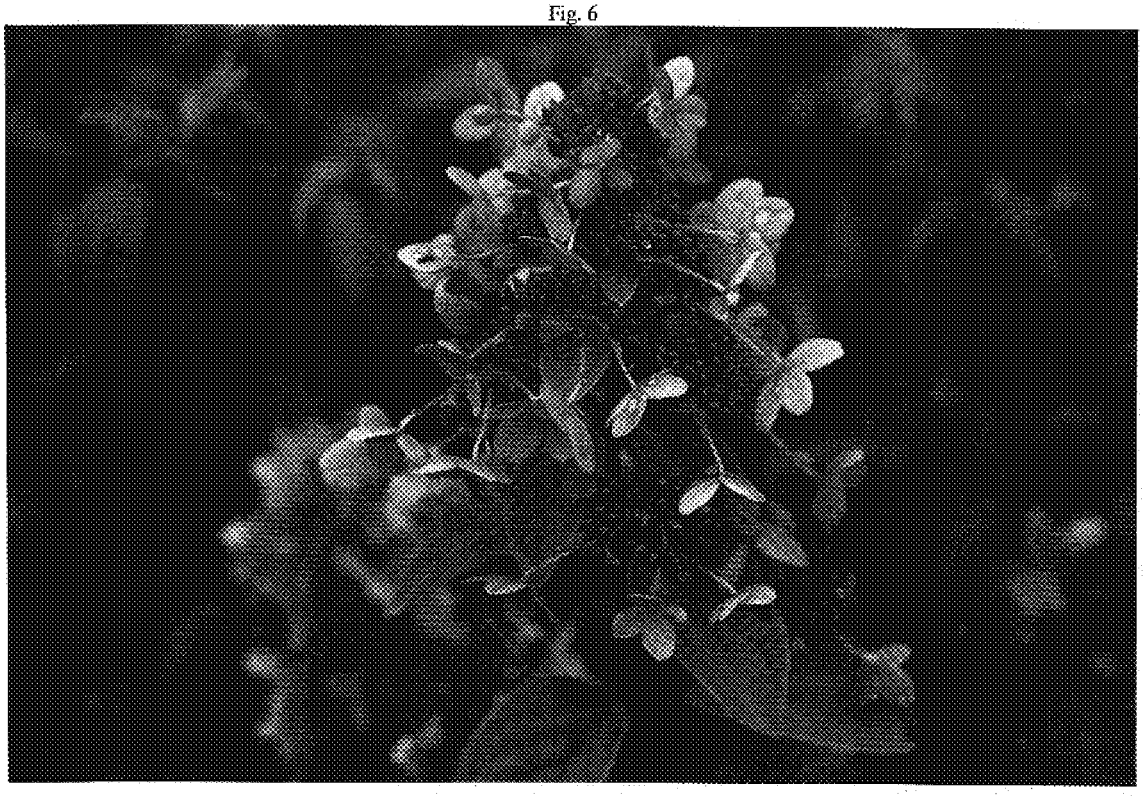
FIG. 6 shows a mature inflorescence of the parent, 'Pink Diamond', showing the openness of the 'Pink Diamond' inflorescence.

A detailed description of *Hydrangea paniculate* 'HYPMAD II' follows. Colors are based on The Royal Horticultural Colour Chart (2001). All measurements/characteristics were taken from 4-year-old plants in the ground of the UGA Horticultural Farms, Athens, Ga., USDA Zone 7. Measurements of leaf/stems and floral characteristics are based on 10 to 20 samples.

Plant:

The plant has a compact, oval, rounded growth habit, with many upright branches from the base, attaining a size of 130 cm high by 170 cm wide after 4 years.

Stems:

Current year stems are round, averaging 5.2 mm in diameter, with no pubescence or exfoliation and are Greyed — Green 197A in color. The average internode length is 5.3 cm. Older stems are up to 23 mm in diameter, rough and Greyed — Green 197A in color.

Vegetative buds:

The imbricate vegetative buds are in an opposite arrangement, 1 per leaf and 2 per node, flat on the stem. They are rounded to globose in shape, 0.5 mm by 1 mm, and have 4 to 6 scales which are Brown 200B in Color.

Flower buds:

The flower buds are round in shape with no pubescence, 4 mm long by 3 mm wide and White 155B in color. They develop in the summer, and time range for showiness is around 8 weeks.

Leaf:

The leaves, in opposite arrangement, are ovate in shape with rounded to acute base and acute apex and finely serrate margin. The mature leaf is 11.2 cm long by 7.7 cm wide, thick and leathery with no wax. It is finely setose on upper and lower surfaces, and heavily setose on lower veins and midrib. The color of the emerging leaf is Yellow — Green 145A on both upper and lower surfaces, maturing to Green 139A on the upper surface and Greyed — Green 191A on the lower. The venation is pinnate, with Yellow — Green 148C veins.

The leaves remain green with no significant fall color changes.

The petioles average 1.6 cm long and 3 mm in diameter, are grooved above and rounded below, finely setose, and are Yellow — Green 148C in color.

Inflorescence:

The bloom period from flower opening to maturity is 2 months, then persisting till damaged by cold. HYPMAD II blooms two weeks later than HYPMAD I.

The paniculate inflorescence, containing an average of 1082 sterile florets (sepals) and fertile flowers, averages 19.7 cm long by 15.2 cm at greatest width.

There are on average 109 inflorescences per plant, one per terminal branch.

Sterile florets:

There are 4 sepals, elliptical to round in shape with obcordate apex and rounded base and entire margin. The texture is smooth with no pubescence. They are 18.4 mm long by 15.7 mm wide. At emergence, the upper surface is Yellow — Green N144A and the lower surface is Yellow — Green 145C, becoming White 155A at full bloom, and Greyed — Purple 186C to 186B to 186A on upper and lower surfaces at maturity.

The peduncle is finely setose and White 155A in color. The average peduncle length is 22 cm.

Fertile flowers:

The petals are ovate in shape, with acute apex, truncate base and an entire margin. They are 4 mm in length by 2 mm wide, with a smooth texture and no pubescence. Their color is White 155A.

The pedicel is 2 mm long, finely setose, and Yellow — White 158D in color.

There are 10 stamens, the anthers being 1 mm long by 1 mm wide and Greyed — Orange 165D in color.

The filament is 4.5 mm long by 0.5 mm wide and White 155B in color.

The superior pistil is globose in shape, 5 mm long by 3 mm wide with no pubescence with both colors, White 155B and Yellow-Green 145D, being individually present.

There are 2 to 3 stigmas per flower, with no pubescence and Greyed — Orange 165A in color.

The style is columnar in shape, 2 mm long with no pubescence and White 155D in color.

There is 1 ovary, rounded in shape, with no pubescence.

Fruit:

The fruit is a dehiscent capsule, ovoid in shape, 4 mm long by 2 mm wide, and maturing from Yellow — Green 144A through Greyed — Orange 177A to Brown 200A in color. They are persistent for 3 to 4 months but are not aesthetic.

Seed:

The seeds are linear in shape, 3 mm long by 0.5 mm wide and Greyed — Orange 164A in color.

I claim:

1. A new and distinct variety of *Hydrangea paniculata* plant substantially as herein described and illustrated.

* * * * *